Aug. 10, 1954 A. J. FRASER Plant Pat. 1,294
HYBRID TEA ROSE PLANT
Filed Oct. 6, 1950
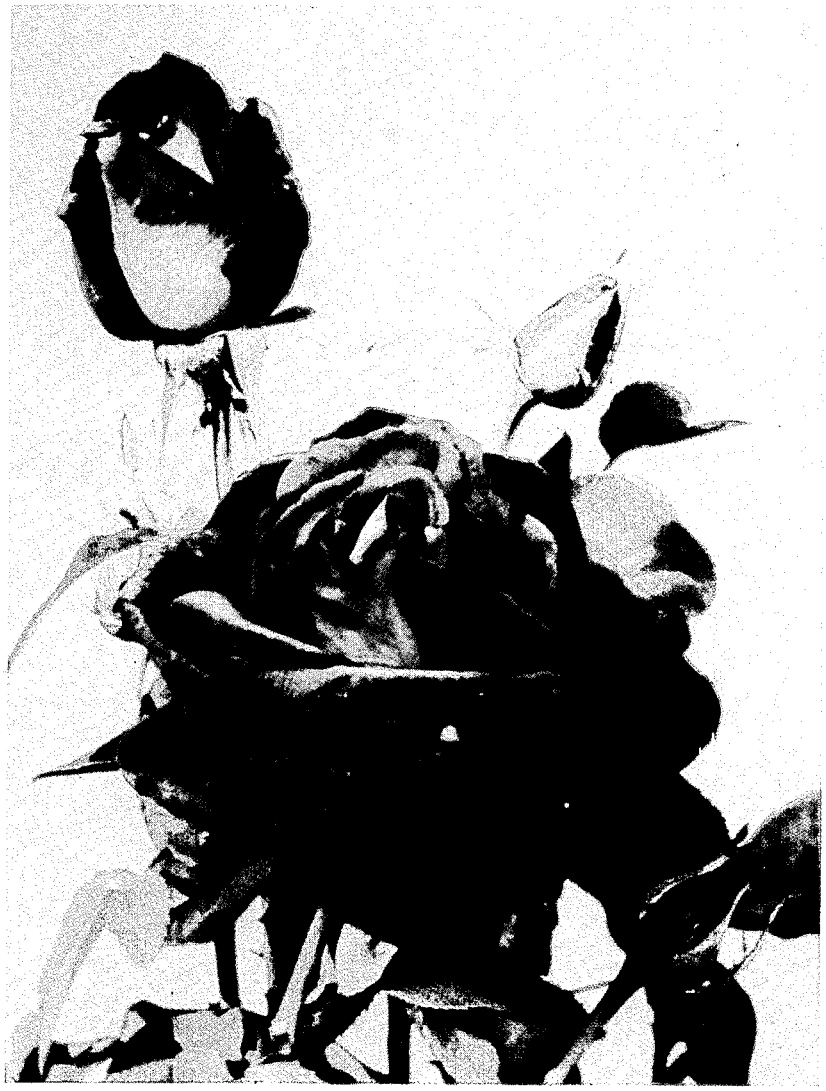
INVENTOR
ALFRED JAMES FRASER
By Linton and Linton
ATTORNEYS Patented Aug. 10, 1954

Plant Pat. 1,294

UNITED STATES PATENT OFFICE 1,294

HYBRID TEA ROSE PLANT

Alfred James Fraser, Queensferry, England, assignor to Bees Limited, Liverpool, England, a British company Application October 6, 1950, Serial No. 188,765

1 Claim. (Cl. 47—61)

My present discovery relates to improvements in hybrid tea rose plants with particular reference to the type used for greenhouse culture.

The new variety originated as a result of my breeding or discovery in my greenhouses, at Sealand, Cheshire, England, as seedlings, the seed parent being "Crimson Glory," Plant Patent No. 105, and the pollen parent being "Madge Whipp" which is unpatented.

The most outstanding characteristics of the present rose plant are: its flower having a deep crimson color with rich velvet-like pile, high-centered bud, blooms large and borne singly 5½ inches to 6½ inches in diameter when fully open displaying broad petals and numerous stamens of golden-yellow coloration; leaves each composed of from five to seven olive green leaflets, oval in shape and with toothed edge; and green twigs bearing straight red triangular thorns and tapering to a point.

The accompanying illustration shows four specimens of the present rose in various stages of opening.

Following is a detailed description of my new variety. Color chart and page references are to "Horticultural Colour Chart" published by the British Colour Council and the Royal Horticultural Society.

*The flower*

Propagation: The rose holds its distinguishing characteristics through succeeding propagations by budding at Sealand, Cheshire, England.

Flowers borne: Three, in regular pyramidal cluster on strong long stems.

Quantity of bloom: Free and abundant outdoors.

Continuity: Intermittent.

Fragrance: Moderate.

Bud: Peduncle long, erect, dark red, chart 824, page 169, with thorns.

*Before calyx breaks.*—Form—size, large; long; pointed. Foliaceous parts extending beyond the tip of the bud equal to one quarter or more of its length.

*As calyx breaks.*—Color—dark red, chart 824, page 169.

*As first petal opens.*—Displaying broad, long and pointed petals. Color outside—light crimson, chart 821/1, page 169. Color inside—dark crimson, chart 824, page 169.

*Opening.*—Opens up well.

Bloom: Size, when fully open, large 5½ inches to 6½ inches.

Bloom petalage: From 20 to 25 petals arranged regularly, numerous stamens of golden yellow coloration, chart 07/1, page 101.

Form: High center at first and remaining high-centered; petals remaining at first tight, but becoming later at maturity tightly rolled outward.

Petals: Thick, with inside shiny, velvety; outside shiny; shape outside, obovate.

This description of a newly opened flower was made from a rose grown outdoors:

Month: July, year, 1949, place Sealand, Cheshire, England.

Outside petals: Outer surface—light crimson, chart 824/1, page 169; inner surface—dark crimson, chart 824, page 169.

Intermediate petals: Outer surface—light crimson, chart 824/1, page 169; inner surface—dark crimson, chart 824, page 169.

Inner petals: Outside surface—light crimson, chart 824/1, page 169; inside surface—dark crimson, chart 824, page 169.

This description is made from a rose which was open for three days outdoors:

Month: July, year 1949, place Sealand, Cheshire, England.

Color of outside petal: Outside surface—light crimson, chart 824/1, page 169; inside surface—dark crimson, chart 824, page 169.

Color of inside petal: Outside surface—light crimson, chart 824/1, page 169; inside surface—dark crimson, chart 824, page 169.

*General color effect.*—Newly opened flower, dark velvety crimson, chart 824, page 169.

*Three days open.*—Varies very little.

*Behavior.*—Drops off cleanly, is affected by wet weather when petals become slightly spotted darker red which is hardly noticeable.

*Flower longevity.*—On bush in garden four days in August, while cut roses kept in living room temperature, 3 days in August.

*Reproductive organs*

Stamens: Medium, arranged regularly about pistils.

Filaments: Short with anthers.

Anthers: Medium size, yellow, chart 07/1, page 101, all open at once.

Pollen: Abundant, gold, chart 07/2, page 101.

Pistils: Many.

Styles: Even.

Hips: Globular, green, 861/1, page 176, smooth, walls thick.

Sepals: Permanent, long, spear shaped, curled.

*The plant*

Type: Hardy; tall bush for garden decoration.
Foliage: Leaves—abundant, large, leathery.
Leaflets: Oval, acute apex, round base.
Margin: Simply serrate.
Color mature: Upper surface—olive green, chart 00962, page 193; under surface—normal green, chart 0960, page 187.
Color of young plant: Upper surface—red, chart 821/1, page 167; under surface—red, chart 821/1, page 167.
Rachis (the supporting stem of the compound leaf): Heavy. Upper surface—smooth and grooved; under surface—hairy.

*Growth*

Habit: Bushy, upright, vigorous.
Canes: Heavy.
Main stems: Greeny brown, chart 0960/3, page 187, streaked with color as shown on chart 00918/3, page 192.
*Thorns.*—Many, long, straight, with broad round base.
*Twigs.*—Green, chart 0960/2, page 187, bearing straight red, chart 00823/3, page 191, triangular thorns tapering to a point.
*Prickles.*—Many, green, chart 0960/2, page 187.
*Hairs.*—Several, green, chart 0960/2, page 187.
Branches: Bright, with touches of green, chart 0960/3, page 187, and brown, chart 00918/3, page 192.
*Thorns.*—Several, long, straight, with broad round base.

*Prickles.*—Several, green, chart 0960/3, page 187.
*Hairs.*—Several, green, chart 0960/3, page 187.
New shoots: Bright, bronze red, chart 821/2, page 167.
*Thorns.*—Many, long and straight, with broad round base.
*Prickles.*—Many, green, chart 0960/3, page 187.
*Hairs.*—Many, green, chart 0960/3, page 187.

I claim:

The new and distinct variety of hardy hybrid tea rose plant as described and illustrated, characterised particularly by its high-centered bud, deep crimson blooms with rich velvet-like pile, borne singly and having large size, 5½ inches to 6½ inches in diameter when fully open displaying broad petals and numerous stamens of golden-yellow coloration; leaves each composed of from five to seven olive green leaflets, oval in shape and with toothed edges, and green twigs bearing straight red triangular thorns and tapering to a point.

References Cited in the file of this patent

UNITED STATES PATENTS

| Number | Name | Date |
|---|---|---|
| Pl. Pt. 367 | Grillo | Mar. 5, 1940 |
| Pl. Pt. 379 | Pahissa | Apr. 6, 1940 |
| Pl. Pt. 452 | Coddington | Feb. 25, 1941 |
| Pl. Pt. 632 | Lammerts | June 27, 1944 |
| Pl. Pt. 778 | Grillo | Jan. 6, 1948 |
| Pl. Pt. 870 | Chase | Sept. 6, 1949 |